United States Patent [19]
Chapel

[11] 4,383,451
[45] May 17, 1983

[54] APPARATUS AND METHOD FOR REMOVING MATERIAL

[76] Inventor: Nimrod T. Chapel, 3804 Green Oaks Way, Edmond, Okla. 73034

[21] Appl. No.: 252,846

[22] Filed: Apr. 10, 1981

Related U.S. Application Data

[62] Division of Ser. No. 113,192, Jan. 18, 1980, Pat. No. 4,274,676.

[51] Int. Cl.³ .............................................. G01N 1/04
[52] U.S. Cl. .............................. 73/864.41; 73/864.91
[58] Field of Search ........... 73/864.41, 864.42, 864.43, 73/864.44, 864.45, 864.51, 864.91; 220/8, 408

[56] References Cited

U.S. PATENT DOCUMENTS

| | | | |
|---|---|---|---|
| 1,495,594 | 5/1924 | Hutchins | 220/8 |
| 1,504,530 | 8/1924 | Thomas | 220/8 |
| 1,821,715 | 5/1932 | Kuchinsky . | |
| 1,847,136 | 3/1932 | Rauberstrauch | 73/864.44 |
| 2,319,023 | 5/1943 | Walker . | |
| 2,463,455 | 3/1949 | Dann . | |
| 2,514,142 | 5/1950 | Reid . | |
| 2,701,557 | 2/1955 | Cooper . | |
| 2,835,246 | 5/1958 | Boettger | 73/864.91 |
| 3,041,793 | 7/1962 | Shimzo . | |
| 3,110,182 | 11/1963 | Moss et al. . | |
| 3,134,127 | 5/1964 | Klein . | |
| 3,146,838 | 9/1964 | Tijann | 73/864.44 |
| 3,162,256 | 12/1964 | Meinecke | 73/864.44 |
| 3,275,180 | 9/1966 | Optner et al. | 220/408 |
| 3,598,446 | 8/1971 | Hatcher . | |
| 3,606,470 | 9/1971 | Blum . | |
| 3,608,968 | 9/1971 | Burnett . | |
| 3,834,198 | 10/1974 | Reynolds . | |
| 3,948,005 | 4/1976 | Whitsett . | |
| 4,027,537 | 6/1977 | Van Doorn . | |

Primary Examiner—S. Clement Swisher
Attorney, Agent, or Firm—E. Harrison Gilbert, III

[57] ABSTRACT

An apparatus and method for removing material from a surface so that the removed material will not escape into the ambient environment are disclosed. The present invention includes a coagulant-applying mechanism for spraying a coating of coagulant on the material to be removed. Also included is a cutter head assembly which is moved along the surface for scraping the material therefrom. So that the scraped, coagulated material may be safely withdrawn to a storage receptacle, the present invention also includes a mechanism which withdraws the loosened, coagulated particles from the cutter head assembly. The system of the present invention incorporating these elements also includes a sampling container for extracting and storing a portion of the subject material for examination thereof.

3 Claims, 7 Drawing Figures

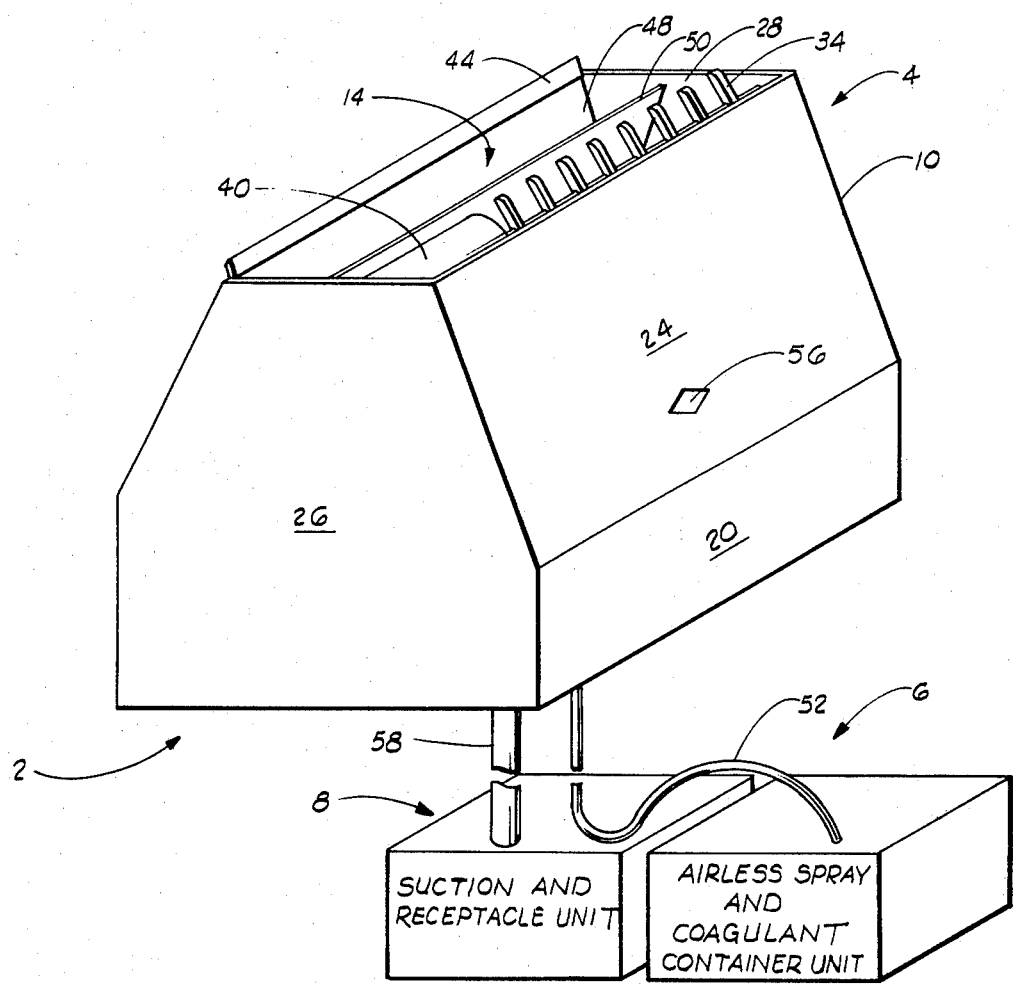
FIG. 1
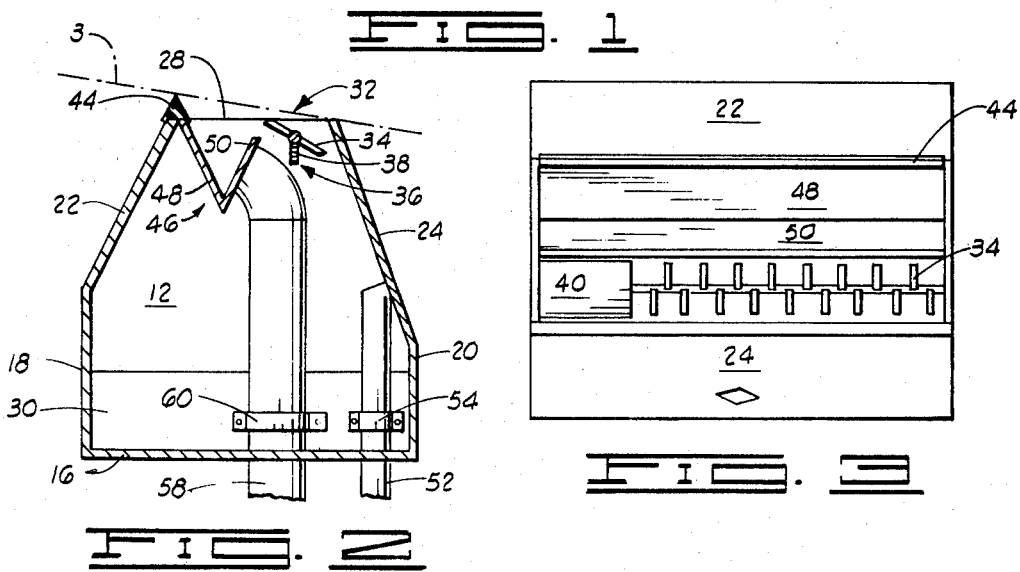
FIG. 2
FIG. 3

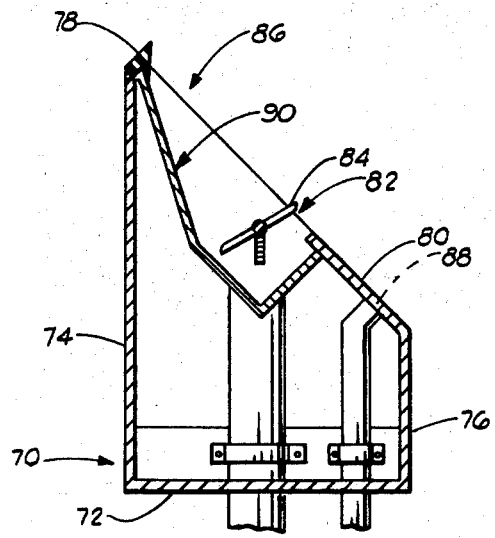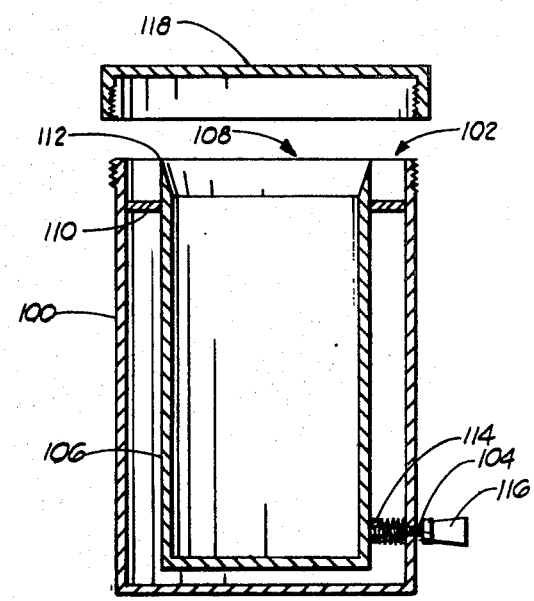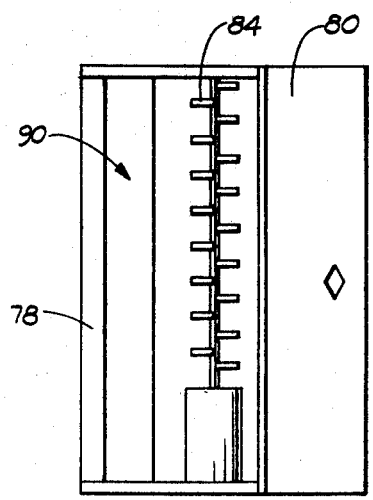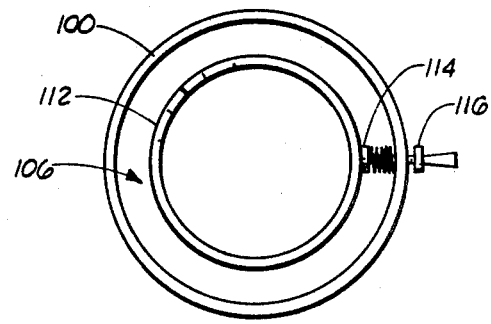

APPARATUS AND METHOD FOR REMOVING MATERIAL

This is a division, of application Ser. No. 113,192, filed Jan. 18, 1980 now U.S. Pat. No. 4,274,676.

BACKGROUND OF THE INVENTION

1. Field of the Invention

This invention relates generally to apparatus and methods for removing material and more particularly, by not by way of limitation, to apparatus and methods for removing asbestos from walls without contaminating the ambient environment.

2. Description of the Prior Art

It is often necessary to remove various materials from their natural or fabricated locations, such as rock formations or interior building walls. For example, it is currently necessary to remove deposits of asbestos found in building materials which have been used in such places as schools. This necessity for asbestos removal has arisen from the discovery that asbestos is, or may be, a carcinogen. Thus, there is the need for an apparatus which can remove the desired materials by cutting, scraping, or otherwise removing, them from the desired locations.

To prevent the removed material from dispersing throughout the ambient environment and thereby possibly causing contamination, such as could occur with particles of asbestos, it is necessary to perform removal without allowing the removed particles arising from the cutting or other removing process to filter into the ambient environment. Thus, there is the need for the apparatus to contain the removed particles, such as by coagulating the particles into a bonded mass, and to withdraw them from the removal area.

Prior to using such an apparatus to remove material from a structure, it is necessary to determine if that particular structure contains any of the material desired to be removed. For example, some materials have the appearance of containing asbestos, but they are in fact non-asbestos materials. Therefore, there is the need for means for sampling the subject structure. This sampling means should provide for the obtaining of uniform bulk samples of the material of the subject structure and should provide for the safe containment of the sample if the material were dangerous.

That there is the general need for an apparatus for cutting or scraping a surface and removing the material therefrom is supported by U.S. Pat. No. 3,843,198 in the name of Reynolds. This patent discloses a rock sampling tool which cuts the rock from a surface and which uses an air stream to reduce dispersal of the resultant dust into the surrounding area.

Although the Reynolds patent discloses such a device, it will be noted that individual particles of dust resulting from the rock cutting operation may escape into the ambient environment without being drawn into the air stream of Reynold's device because of the tendency of certain substances to scatter or disperse upon being cut, scraped, or otherwise loosened. This is a critical shortcoming when the material to be removed is asbestos, for example, because the escape of even a few particles of asbestos can create a serious health hazard. Furthermore, the Reynolds reference fails to disclose a sampling container for extracting and safely holding a portion of the substance so that it can be analyzed. Therefore, I believe that the prior art fails to provide an apparatus for removing a material, such as asbestos, from a structure, such as the interior walls of a school, in which the material is located without allowing particles of the removed material to escape into the ambient environment.

SUMMARY OF THE INVENTION

The present invention overcomes the above-noted and other shortcomings of the prior art by providing a novel, useful and non-obvious apparatus and method for removing material. This invention can be used to remove materials from the structures in which the materials are used. In particular, the present invention provides an apparatus for removing asbestos without allowing a significant amount, if any, of the removed particles to filter into the ambient environment. The method and apparatus provide for containing the removed particles and for withdrawing these particles from the area from which they are removed.

The present invention also provides means for sampling and safely containing portions of the material for testing prior to the removal thereof.

Broadly, the present invention provides an apparatus for removing material from a surface comprising means for applying a coating of a coagulant to the material to be removed; means, associated with the coagulant applying means, for scraping the surface to loosen the material therefrom; and means, associated with the scraping means, for withdrawing the loosened material from the scraped surface.

More particularly, the coagulant applying means includes means for airlessly spraying a substance and a coagulant container coupled with the airlessly spraying means so that the coagulant is extracted from the container by the spraying means and airlessly sprayed on the material to be removed.

The scraping means includes a housing and a cutter member rotatably connected to the housing for striking the material to be removed when the housing is moved adjacent the surface.

The withdrawing means includes means for creating a suction and a conduit extending from the suction means to a position proximate the cutter member for receiving the loosened material and conveying it to the suction means.

The present invention also provides a system for determining the nature of a material and for removing the material when it is determined to be of a predetermined nature. This system includes means for sampling the substance to obtain a portion for testing the composition thereof, means for testing the sampled portion, and the coagulant applying means, scraping means, and withdrawing means previously mentioned.

The method of the present invention includes the steps of applying a coating of the coagulant to the material to be removed, scraping the surface to loosen the material therefrom, and withdrawing the loosened, coagulant-coated material from the surface and surrounding environment.

Therefore, from the foregoing it is a general object of the present invention to provide a novel, useful and non-obvious method and apparatus for removing material. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 1 is an oblique and block illustration of the removal apparatus of the present invention.

FIG. 2 is a sectional end elevation view of the cutter head assembly shown in FIG. 1.

FIG. 3 is a top plan view of the cutter head assembly shown in FIG. 1.

FIG. 4 is a sectional and elevation view of a second embodiment of a cutter head assembly of the present invention.

FIG. 5 is a top plan view of the cutter head assembly shown in FIG. 4.

FIG. 6 is a sectional elevational view of the sampling container of the present invention.

FIG. 7 is a top plan view of the sampling container shown in FIG. 6.

DETAILED DESCRIPTION OF THE PREFERRED EMBODIMENTS OF THE INVENTION

With reference now to the drawings and in particular to FIGS. 1-3, a preferred embodiment of the removal apparatus constructed in accordance with the present invention will be described. In FIG. 1 the apparatus for removing material from a surface, which apparatus is particularly for removing asbestos from a surface 3 and for preventing the removed asbestos particles from escaping into the ambient environment by using a coagulant, is generally identified by the reference numeral 2. The apparatus 2 includes means 4 for scraping the surface to loosen the material therefrom, means 6 for applying a coating of a coagulant to the material to be removed, and means 8 for withdrawing the loosened, coagulant-coated material from the scraped surface.

In the preferred embodiment, the scraping means 4 is a cutter head assembly comprising a housing 10. As shown in FIG. 2, the housing 10 includes a cavity 12 extending into the housing from an opening 14 formed in the wall of the housing 10. In the preferred embodiment the housing 10 is to be constructed of a light-weight stainless steel and is from six to twenty-four inches long, twelve inches wide and twelve inches high. However, the material and size may be of any appropriate nature suitable for practicing the present invention.

For the preferred embodiment shown in FIGS. 1-3, the housing 10 includes a bottom wall 16, a first side wall 18 vertically extending from one edge of the bottom wall 16 and a second side wall 20 vertically extending from the edge of the bottom wall 16 opposite that edge from which the first side wall 18 extends. The housing 10 further includes a third side wall 22 angularly extending from the edge of the first side wall 18 opposite the bottom wall 16 inwardly toward the opening 14 defined adjacent the top edge of the third side wall 22. The housing 10 also includes a fourth side wall 24 extending angularly from the edge of the second side wall 20 opposite the bottom wall 16 inwardly toward the opening 14 defined adjacent the top edge of the fourth side wall 24. Enclosing the ends of the connected side walls and bottom wall are a first end wall 26 and a second end wall 28. This assemblage of the bottom wall 16, the side walls 18, 20, 22 and 24, and the end walls 26 and 28 defines the cavity 12. Disposed within the cavity 12 and extending between the first side wall 18 and the second side wall 20 is a support plate 30.

The cutter head assembly also includes a cutter member 32 having one or more blades 34 extending therefrom. The member 32 is rotatably connected to the end walls 26 and 28 of the housing 10 so that the blade 34 extends through the opening 14 when the member 32 rotates. Having the blade 34 extend through the opening permits it to scrape the surface from which the desired material is to be removed. That is, as the housing 10 is moved along the surface from which the material is to be removed, the cutter member 32 rotates and the blade 34 strikes the material on and below the surface to thereby dislodge the material therefrom. The blade or blades 34 may be placed on the cutter member 32 in any appropriate position, such as in the staggered, or offset, configuration shown in FIG. 3.

FIG. 2 also shows that the present invention includes mounting means having a biasing element for yieldably receiving the cutter member 32. In particular the preferred embodiment mounting means includes a groove formed in each of the end walls 26 and 28 of the housing 10 to extend vertically downward from the rotatably mounted cutter member 32. Located within each of the grooves 36 is a biasing element such as a spring 38. One end of the spring 38 is held adjacent the bottom surface of the groove 36 and the opposite end of the spring 38 yieldably retains the rotatably mounted cutter member 32 thereon. Thus, the mounting means permits the cutter member 32 to be vertically displaced by a downwardly acting force which exceeds the biasing force of the spring 38. This means for permitting the vertical displacement of the cutter member helps keep the cutter member 32 from binding when irregularities are encountered on the surface along which the cutter head assembly is moved. In the preferred embodiment the mounting means permits approximately one inch of vertical displacement.

The present invention further includes drive means for rotating the cutter member. In particular the drive means includes a motor 40 as represented in FIG. 1. The energization of the motor 40 can be from a battery pack located within the cutter head assembly or it can be provided by another energization means remotely located but connected to the motor via conductors extending therebetween.

FIG. 2 further shows that the preferred embodiment shown therein includes a resilient member 44 extending along the top edge of the third side wall 22. Particularly, the resilient member 44 is a rubber strip extending along one edge of the opening 14 and above the plane containing the opening 14, i.e., above the outer surface of the wall of the housing in which the opening 14 is defined. The resilient member 44 provides means for sealing the cutter head assembly against the surface from which the material is to be removed so that material will not escape as the cutter member 32 rotates its blade 34 toward the member 44. In the preferred embodiment the resilient member 44 is a three-quarter-inch rubber strip extending one-half inch above the top surface of the housing 10 and along the entire length thereof.

As just described, the resilient member 44 provides a seal between the cutter head assembly and the surface which is being scraped so that the loosened material will not pass between a gap which might otherwise be formed between the surface and the head assembly. By so sealing this head/surface interface, the loosened material is caused to fall into a trough 66 which is connected to the side wall 22 so that the trough extends into the cavity 12 below the cutter member 32. Thus, as the cutter member 32 and blade 34 rotate to cut into the surface 3, the loosened material scraped from the surface is collected in the trough 46. In the preferred embodiment the trough 46 extends approximately three inches below the top edge of the side wall 22 to which the upper edge of the trough 46 is connected. As shown in FIG. 2, the preferred embodiment trough 46 has a V-shaped configuration as defined by the connection of a first leg 48 and a second leg 50.

As depicted in FIG. 1, the means for applying a coating of coagulant to the material includes means for airlessly spraying a substance and also includes a container of the coagulant coupled with the airlessly spraying means so that the coagulant is extracted from the container by the spraying means and airlessly sprayed on the material to be removed.

The airlessly spraying means includes a substance discharging means which may be of any suitable type as known in the art for airlessly spraying a substance. As shown in FIG. 1, coupled with and extending from the discharging means is a first conduit 52 of any type suitable for use in an airless spraying system. The discharging end of the first conduit 52 is connected to the housing 10. In particular, as shown in FIG. 2, the conduit 52 is passed through an opening in the bottom wall 16 and is connected to the plate 30 by means of a bracket 54 so that the discharging end of the conduit 52 is held in position adjacent an outlet port 56, defined in the fourth side wall 24, to airlessly discharge the coagulant pumped by the discharging means therethrough.

The coagulant container is of any suitable type as known in the art. The coagulant is a stabilizing substance which causes the particles of the removed material to become bonded as integral parts of a bonded mass which will not disperse into the ambient environment, but rather will fall into the cavity 12 of the housing 10. One example of the coagulant is a suitable mixture of a high molecular weight polyamide and water.

The means for withdrawing the loosened material from the scraped surface, which means is associated with the scraping means 4, includes means for creating a suction, such as any appropriate vacuum device as known in the art, and a conduit 58 coupled to the suction creating means and extending therefrom, through an opening in the bottom wall 16, and to a position proximate the cutter member 32 for receiving the loosened material and conveying it to a receptacle contained within the suction means. As shown in FIG. 2, the inlet end of the conduit 58 is connected to the trough 46, and in particular to the leg 50 thereof, so that as the coagulated particles of the removed material fall into the trough 46 they are withdrawn therefrom by means of a suction generated by the suction creating means. The conduit 58 may be of any suitable type, but in the preferred embodiment it is contemplated to be a flexible tube having a diameter of from approximately two to three inches. The conduit 58 is held in position adjacent the trough 46 by means of a bracket 60 which clamps the conduit 58 to the plate 30. Although the preferred embodiment shows the conduit 58 connected to the trough 46, it is to be noted that the present invention can properly operate by merely disposing the inlet end of the conduit 58 in the cavity 12 and allowing the removed particles to fall into the cavity whereby they are withdrawn through the conduit 58 under suction provided by the suction creating means.

Referring to FIGS. 4 and 5, a second preferred embodiment of the scraping means, or cutter head assembly, of the present invention will be briefly discussed. In this embodiment, the cutter head assembly includes a housing 70 comprising a bottom wall 72, a first side wall 74 extending vertically from one of the edges of the bottom wall 72, and a second side wall 76 extending vertically from the opposite edge of the bottom wall 72. The housing 70 also includes a resilient member 78 and a first angular side wall 80 extending from the first side wall 74 and the second side wall 76, respectively. The resilient member 78 and the angular sidewall 80 correspond to elements 44 and 24, respectively, of the first embodiment described above. The FIG. 4 embodiment also includes a cutter member 82 having one or more blades 84 extending therefrom similar to the corresponding elements in the preceding embodiment. However, in the FIG. 4 embodiment the cutter element 82 and the blade 84 are disposed within the housing 70 so that the blade 84 extends through an opening 86 defined between the unconnected edges of the member 78 and side wall 80 in the same plane as an outlet port 88 defined in the side wall 80 and through which the coagulant is discharged by the coagulant applying means of the present invention. In other words, the coagulant is discharged and the cutting is performed along the same planar surface of the housing 70 of the second preferred embodiment of the present invention. Also shown in FIG. 4 is a trough 90 shown extending from the side wall 74 to the side wall 80 beneath the cutter member 82.

With reference to FIGS. 6 and 7, the overall system for determining the nature of the material and for removing the material when it is determined to be of the appropriate nature will be described. This system includes means for sampling the substance to obtain a portion for testing the composition thereof and means for testing the sampled portion. This system also includes the previously described elements.

In FIG. 6 the sampling means is shown to include a first container 100 having an open end 102 and an aperture 104 extending through the wall of the container. The sampling means also includes a second container 106 having an open end 108. The second container 106 is slidably engaged within the first container 100 for slidable extension through the open end 102 thereof. In the preferred embodiment this sliding engagement is effected by means of an annular alignment collar 110 which is connected to the interior surface of the container 100 for retaining the container 106 in spaced relation to the side wall of the first container 100.

The container 106 has a sharp edge 112 encircling the opening 108. The purpose of the sharp edge 112 is to cut into the surface of the substance to be sampled when the container 106 has been extended from the first container 100. After the sample has been cut and retained within the second container 106, the second container 106 is moved back into the position within the first container 100 shown in FIG. 6. The second container 106 further includes a latch-receiving member 114 disposed thereon in alignment with the aperture 104 of the first container 100. In the preferred embodiment of FIG. 6, this latch-receiving member 114 is a notch formed in the outer side of the wall of the container 106.

The sampling means further includes a latch means 116 extending through the aperture 104 of the first container 100 in releasable abutment with the latch-receiving member 114 of the second container 106. When the latch means 116 abuts the receiving member 114, the second container 106 is prevented from slidably extending from the first container. The latch means 116 may include a pin and an associated spring which retains the pin in abutment with the latch-receiving member 114 of the second container 106. When the container 106 is desired to be extracted from the container 100, the pin can be disengaged from its abutment with the latch-receiving member 114 and the container 106 pulled from the container 100.

The sampling means further includes a closure means 118, such as a screw-on lid, for closing the open end of the first container 100 when the second container 106 is positioned within the container 100 as shown in FIG. 6.

The means for testing the sampled material contained within the second container 106 after the sample has been cut from the surface by the cutting edge 112 thereof includes any appropriate equipment for analyzing the composition of the sampled material. For example, to determine if the material is asbestos, polarized light microscopy apparatus or X-ray diffraction equipment may be used as is known in the art.

With reference to all the drawings, the operation of the present invention will be described. Initially, the nature of the material in question must be determined. A sample of the subject material is obtained by releasing the latch means 116 from its engagement with the latch-receiving member 114, extracting the container 106 from the container 100, digging the sharp edge of the container 106 into the substance to thereby cut a sample, collecting the cut sample in the container 106, and retracting the container 106 into the container 100 and capping it with the closure means 118.

This sample is then appropriately analyzed with the appropriate testing means. If the test shows that the material contains the material to be removed, such as asbestos, then the removal apparatus is utilized to remove the material.

With reference to the embodiment shown in FIGS. 1-3, the side 24 of the cutter head assembly is first moved adjacent the surface from which the particular material is to be removed. During this step of moving the cutter head assembly, the coagulant is discharged from the discharging means through the conduit 52 and the outlet port 56 so that a coating of the coagulant is applied to the surface containing the material to be removed. After the material has been coated with the coagulant, the top portion of the cutter head assembly is moved adjacent the surface so that the cutter member 32 and the blade 34 extending therefrom engage the surface to cut, and thereby loosen, the material therefrom. During this cutting step the resilient member 44 is maintained in engagement with the surface to insure that the loosened, coagulant-covered material falls into the cavity 12 of the housing 10. As the cutter blades 34 loosen the material and the material falls into the cavity 12, the trough 46 collects this material so that it can be withdrawn from the cutter head assembly by means of the conduit 54 and the suction creating means connected thereto. Thus, as the loosened material falls into the cutter head assembly, it is withdrawn into a receptacle provided within the suction creating means.

When the cutting process is completed, all the loosened, coagulant-coated material is contained in the receptacle of the suction means. Therefore, by first applying the coagulant to the material to be removed, and then loosening it from its location, the loosened particles are prevented from escaping into the ambient environment and thus are prevented from creating possible health hazards if the loosened material is of a possibly dangerous nature, as with asbestos.

The embodiment illustrated in FIGS. 4 and 5 operates similarly to the one described in FIGS. 1-3. However, one difference is that both the coagulant application and the material cutting steps are performed substantially simultaneously because both of these operations are performed by means disposed along a single surface of the cutter head assembly.

Thus, the present invention of an apparatus and method for removing material is well adapted to carry out the objects and attain the ends and advantages mentioned above as well as those inherent therein. While preferred embodiments of the invention have been described for the purpose of this disclosure, numerous changes in the construction and arrangement of parts can be made by those skilled in the art, which changes are encompassed within the spirit of this invention as defined by the appended claims.

What is claimed is:

1. A system for removing a substance, comprising:
   sampling means for sampling the substance to obtain a portion for testing the composition thereof, said sampling means including:
      a first open-ended container having an aperture extending through the side wall thereof;
      a second open-ended container engaged within said first container for slidable extension through the open end thereof, said second container having a latch-receiving member disposed thereon in alignment with the aperture of said first container;
      latch means extending through the aperture of said first container in releasable abutment with the latch-receiving member of said second container for preventing said second container from slidably extending from said first container when said latch means abuts the latch-receiving member; and
      closure means for closing the open end of said first container;
   coagulent applying means for applying a coating of a coagulant to the substance to be removed when the sampled portion is a predetermined type of substance;
   scraping means, associated with said coagulant applying means, for scraping the surface to loosen the substance therefrom; and
   means, associated with said scraping means, for withdrawing the loosened substance from the scraped surface.

2. A substance sampling apparatus, comprising:
   a first open-ended container having an aperture extending through the wall thereof;
   a second open-ended container having a cutting means adjacent said open end engaged within said first container for slidable extension through the open end thereof, said second container having a latch-receiving member disposed thereon in alignment with the aperture of said first container;
   latch means extending through the aperture of said first container in releasable abutment with the latch-receiving member of said second container for preventing said second container from slidably extending from said first container when said latch means abuts the latch-receiving member; and
   closure means for closing the open end of said first container.

3. A system for removing asbestos, comprising:

sampling means for sampling a substance to obtain a portion for testing to determine if the substance is asbestos, said sampling means including:
- a first open-ended container having an aperture extending through a side wall thereof;
- a second open-ended container disposed within said first container for slidable extension through the open end of said first container, said second container having a latch-receiving member disposed thereon;
- latch means extending through the aperture of said first container in releasable association with the latch-receiving member of said second container for preventing said second container from slidably extending from said first container when said latch means is releasably associated with the latch-receiving member; and
- closure means for closing the open end of said first container;

coagulant applying means for applying a coating of a coagulant to the substance to be removed when the sampled portion is asbestos;

scraping means, associated with said coagulant applying means, for scraping the surface to loosen the substance therefrom; and means, associated with said scraping means, for withdrawing the loosened substance from the scraped surface.

* * * * *